United States Patent [19]

Nicol et al.

[11] Patent Number: 5,607,929

[45] Date of Patent: Mar. 4, 1997

[54] ANTIVIRAL DIBENZOTHIAZEPINONE DERIVATIVES

[75] Inventors: Robin H. Nicol, London; Martin J. Slater; Simon T. Hodgson, both of Beckenham, all of England

[73] Assignee: Glaxo Wellcome Inc., Research Triangle Park, N.C.

[21] Appl. No.: 140,120

[22] PCT Filed: May 1, 1992

[86] PCT No.: PCT/GB92/00805

§ 371 Date: Dec. 6, 1993

§ 102(e) Date: Dec. 6, 1993

[87] PCT Pub. No.: WO92/19277

PCT Pub. Date: Nov. 12, 1992

[30] Foreign Application Priority Data

May 2, 1991 [GB] United Kingdom ............... 9109557

[51] Int. Cl.$^6$ ........................ A01N 43/00; A61K 31/55; C07D 281/16
[52] U.S. Cl. ............................. 514/211; 540/488
[58] Field of Search ................. 540/488; 514/211

[56] References Cited

U.S. PATENT DOCUMENTS

| 3,367,930 | 2/1968 | Schmuts et al. | 540/488 |
|---|---|---|---|
| 3,541,085 | 11/1970 | Sheeley et al. | 540/488 |
| 3,853,882 | 12/1974 | Szmuskovicz | 540/488 |
| 3,887,575 | 6/1975 | Hester, Jr. et al. | 540/488 |
| 4,002,639 | 1/1977 | Vogt | 540/488 |
| 4,163,785 | 8/1979 | Hoffmann et al. | 540/488 |
| 4,263,207 | 4/1981 | Rokach et al. | 540/488 |
| 4,728,735 | 3/1988 | Belanger et al. | 540/488 |

FOREIGN PATENT DOCUMENTS

| 225894 | 10/1985 | Czechoslovakia | 540/488 |
|---|---|---|---|
| 0240228 | 10/1987 | European Pat. Off. | 540/488 |
| 279425 | 8/1988 | European Pat. Off. | 540/488 |
| 0282236 | 9/1988 | European Pat. Off. | 540/488 |
| 0292824 | 11/1988 | European Pat. Off. | 540/488 |
| 0357043 | 3/1990 | European Pat. Off. | 540/488 |
| 0384522 | 8/1990 | European Pat. Off. | 540/495 |
| 0393604 | 10/1990 | European Pat. Off. | 540/495 |
| 0393530 | 10/1990 | European Pat. Off. | 540/495 |
| 0393529 | 10/1990 | European Pat. Off. | 540/495 |
| 0413300 | 2/1991 | European Pat. Off. | 540/488 |
| 0415304 | 3/1991 | European Pat. Off. | 340/488 |
| 0415303 | 3/1991 | European Pat. Off. | 540/488 |
| 417534 | 3/1991 | European Pat. Off. | 540/485 |
| 0419861 | 4/1991 | European Pat. Off. | 340/488 |
| 0429987 | 6/1991 | European Pat. Off. | 540/495 |
| 1817016 | 8/1969 | Germany | 540/488 |
| 2030714 | 2/1971 | Germany | 540/488 |
| 2301399 | 8/1973 | Germany | 540/488 |
| 2306762 | 8/1973 | Germany | 540/488 |
| 2316438 | 10/1973 | Germany | 540/488 |
| 2546822 | 4/1977 | Germany | 540/488 |
| 45-16951 | 6/1970 | Japan | 540/488 |
| 476753 | 9/1969 | Switzerland | 540/488 |
| 585222 | 2/1977 | Switzerland | 540/488 |
| 1156782 | 7/1969 | United Kingdom | 548/488 |
| 1384991 | 2/1975 | United Kingdom | 540/488 |
| 1403275 | 8/1975 | United Kingdom | 540/488 |
| 1480553 | 7/1977 | United Kingdom | 540/488 |
| 8806449 | 3/1988 | United Kingdom | 540/495 |
| WO89/10369 | 11/1989 | WIPO | 540/522 |

OTHER PUBLICATIONS

R. Pauwls, Nature, vol. 343, pp. 470–473, "Potent and Selective inhibition of HIV–1 replication in vitro by a novel series of TIBO derivative," (1990).

N. Rasanu, Rev. Chim, vol. 20(3), pp. 175–176, "Chimia tioxantonei. Transpozitia Beckman a oximei tioxantonei si oximei tioxanton–5,5–dioxidului," 1969.

A. H. Corwin, A. B. Chivvis, and C. B. Storm, Chemical Abstract, vol. 62, pp. 14681–14684, "Seven– and Higher––Membered Rings," (1965).

J. Schmutz, F. Kunzle, F. Hunziker and A. Burki, Helvetica Chimica Acta, vol. 48, No. 38, pp. 336–347, "Neue Synthese von Lactamen der Dibenz[v,f]–1, 4–thiazepin–, –oxazepin und Dibenz[b,e]–azepin–Reihe," (1965).

P. Catsoulacos, Bulletin de la Societe Chimique de France, No. 6, pp. 2136–2137, "Synthese de derives du dibenzo[b, f] thiazein–1,4 one–10 dioxyde–5,5," (1973).

D. Besanty, J. Mayrargue, G. E. Moussa, M. E. Shaaban, P. Gayral, M. Miocque, Eur. J. Med. Chem, vol. 23, pp. 403–405, "Synthese de benzo et dibenzothiazepines nitrees a visee anti–parasitaire," (1988).

(List continued on next page.)

Primary Examiner—Robert T. Bond
Attorney, Agent, or Firm—Nixon & Vanderhye

[57] ABSTRACT

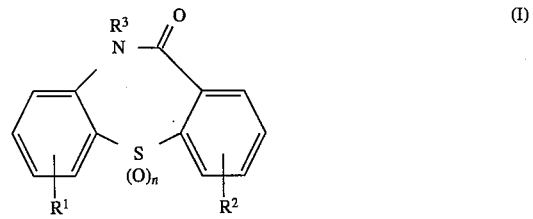

Compounds of formula (I) wherein n is 0, 1 or 2; and $R^1$ and $R^2$, which may be the same or different, each represent one or more ring substituent(s) selected from: hydrogen, hydroxy, halogen, cyano, nitro, $C_{1-6}$alkyl, $C_{3-6}$cycloalkyl or $C_{1-6}$alkoxy (where the alkyl or cycloalkyl moiety may be optionally substituted by one or more substituents selected from halogen atoms and hydroxyl groups); —$NR^4R^5$ where $R^4$ and $R^5$, which may be the same or different, each represent hydrogen or $C_{1-6}$alkyl; —$S(O)_mR^6$, where m is 0, 1, 2 or 3 and $R^6$ represents hydrogen, $C_{1-6}$alkyl or $C_{3-6}$cycloakyl; —$SO_2NR^4R^5$ where $R^4$ et $R^5$ are each as defined above; phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and —$CO_2H$ or —$COR^7$ where $R^7$ is $C_{1-6}$alkyl or $C_{3-6}$cycloalkyl; $R^3$ represents hydrogen or $C_{1-4}$alkyl; and esters, salts and other physiologically functional derivatives thereof; show activity as antiviral agents, for example against HIV. Certain of the compounds are novel.

6 Claims, No Drawings

OTHER PUBLICATIONS

D. Hellwinkel, R. Lenz and F. Lammerzahl, *Tetrahedron*, vol. 39, No. 12, pp. 2073–2084, "Heterocyclic Syntheses via Carbanionically Induced Rearrangement Reactoins" (1983).

N. Kamigata, S. Hashimoto, M. Kobayashi and H. Nakanishi, *The Chemical Society of Japan*, No. 58, pp. 3131–3136, "Photochemical Ring–expansion Reaction of 1,2–Benzisothiazolinones," (1985).

Z. Polivka, J. Holubek, E. Svatek, A. Dlabac, D. Pucek, Z. Z. Sedivy and M. Protiva, *Collection Czechoslovak Chem Commun.*, vol. 48, pp. 1465–1476, "3–(4–Methyliperazino)Dibenzo[b,f]–1,2,4–Triazolo[4,3–d]–1,4–Thiazepine and its 6–Chloro and 12–Chloro Derivatives"; Synthesis and Pharmacology, (1983).

J. Joshi, B. C. Joshi and F. S. K. Barar, *Pharmazie*, No. 44, pp. 265–267, "Synthesis and Pharmacological evaluation of triazolo derivatives of 8–amino–10, 11–dihydro–dibenzo[b,e]1,4–thiazepin–11–one," (1989).

O. F. Bennett, J. Johnson and J. Tramondozzi, *Organic Preparations and Procedures, Int.*, 6(6), pp. 287–293, "Synthesis of 2–Methoxydibenzo [b,f] (1,4)–Thiazepin–11 (10H) –One–5, 5–Dioxide," (1974).

N. Kamigata, S. Hashimoto and M. Kobayashi, *Sulfur Letters*, vol. 2(1), pp. 17–22, "On Direct Photo–Oxidation of Benzisothiazol–3 (2H)–Ones in the Presence of Oxygen," (1984).

G. P. Dhareshwar and B. D. Hosangadi, *Indian J. Chem*, vol. 15B, pp. 963–964, "Studies in Amination & Intramolecular Amidation Reactions with Polyphosphoric Acid: Synthesis of 2–Aminodiphenyl Sulphone, Dibenzo [b,f][1,4] thiazepin–11(10H)–one–5,5–dioxide & Dibenz[b,f][1,4] oxazepin–11(10H)–one," (1977).

N. Kamigata, S. Hashimoto, S. Fujie, and M. Kobayashi, *J. Chem. Soc., Chem. Commun.*, pp. 765–766, "Photoisomerization of 2–Aryl–1,2–benzisothiazol–3(2H)–ones," (1983).

O. F. Bennett, J. Johnson and S. Galletto, *Journal of Heterocyclic Chemistry*, vol. 12, pp. 1211–1213, "A Novel Synthesis of Dibenzo [b,f][1,4]thiazepin–11(10H)one 5,5–Dioxides," (1975).

B. C. Joshi and J. Pande, *Chemistry and Industry*, pp. 825–826, "Synthesis and structural studies of 9–amino–10, 11–dihydro–5H–dibenzo(b,e)(1,4)thiazepine 11–one," (1985).

K. Nagarajan, C. L. Kulkarni, A. Venkateswarlu and R. K. Shah, *Indian Journal of Chemistry*, vol. 12, pp. 258–262, "Condensed Heterotricycles: Dibenz [b,f][1,4] oxazepines–11(10H)–thiones, 11–Substituted Dibenze[b,f][1,4]oxazepines & Dibenz[b,f][1,4]thiazepin Analogues," (1974).

K. Nagarajan, C. L. Kulkarni, and A. Venkateswarlu, *Indian Journal of Chemistry*, vol. 12, pp. 247–251, "Condensed Heterotricycles: Beckmann Rearrangement of Xanthone & Thioxanthone Oximes as a Route to Dibenz[b,f][1,4]–oxazepines & Thiazepines," (1974).

K. Nagarajan, A. Venkateswarlu, C. L. Kulkarny and R. K. Shah, *Indian Journal of Chemistry*, vol. 12, pp. 227–235, "Condensed Heterotricycles: Synthesis of Dibenz[b,f][1,4] oxazepines, Dibenz[b,f][1,4]thiazepins and Dibenz[b,f][1,4] diazepines by Cyclization of 2–Halo–2'–hydroxy(mercato/amino)benzanilides," (1974).

J. Schmutz, F. Kunzle, F. Hunziker and R. Gauch, *Helvetica Chimica Acta*, vol. 50(1), pp. 245–254, "Uber in 11–Stellung amino–substituierte Dibenzo[b,f]–1,4–thiazepine und –oxazepine," (1967).

P. Catsoulacos, *Journal of Heterocyclic Chemistry*, vol. 7(2), pp. 409–411, "Synthesis of Substituted Dihydrodibenzothiazepines and Related Compounds," (1970).

S. Palazzo, L. I. Giannola and S. Curonna, *Journal of Heterocyclic Chemistry*, vol. 11(5), pp. 839–841, "The Behaviour of some Thioxanthene and Thiathrene Derivatives with Hydrazoic Acid," (1974).

N. R. Shete, *Indian J. Chem.*, vol. 21B, pp. 581–582, "Synthesis of 11–Oxo & 11, 11–Diphenyl Derivatives of Dibenzo [b,f][1,4] thiazepines, Dibenzo[b,f][1,4]–oxazepines & Dibenzo[b,e][1,4]diazepines," (1982).

ANTIVIRAL DIBENZOTHIAZEPINONE DERIVATIVES

The present invention relates to the use of certain dibenzothiazepinones as antiviral agents.

A group of dibenzothiazepinone derivatives has now been found which show activity as antiviral agents. Thus, according to one aspect, the present invention provides the use of compounds of formula (I)

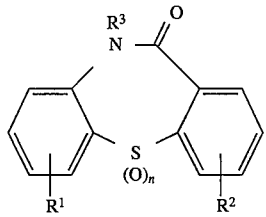

wherein:

n is 0, 1 or 2; and $R^1$ and $R^2$, which may be the same or different, each represent one or more ring substituent(s) selected from:
hydrogen, hydroxy, halogen, cyano, nitro, $C_{1-6}$alkyl, $C_{3-6}$cycloalkyl or $C_{1-6}$alkoxy (where the alkyl or cycloalkyl moiety may be optionally substituted by one or more substituents selected from halogen atoms and hydroxyl groups);
—$NR^4R^5$ where $R^4$ and $R^5$, which may be the same or different, each represent hydrogen or $C_{1-6}$alkyl;
—$S(O)_mR^6$, where m is 0, 1, 2 or 3 and $R^6$ represents hydrogen, $C_{1-6}$alkyl or $C_{3-6}$cycloalkyl;
—$SO_2NR^4R^5$ where $R^4$ and $R^5$ are each as defined above;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$CO_2H$ or —$COR^7$ where $R^7$ is $C_{1-6}$alkyl or $C_{3-6}$cycloalkyl;

$R^3$ represents hydrogen or $C_{1-4}$alkyl;

or an ester, salt or other physiologically functional derivative thereof, for the manufacture of a medicament for the treatment of a virus disease.

According to one embodiment, the invention provides the use of compounds of formula (I) as defined above in which $R^3$ represents hydrogen for the manufacture of a medicament for the treatment of a virus disease.

As used herein the term "alkyl" as a group or part of a group means a straight or branched chain alkyl group. Such alkyl groups preferably have 1 to 3 carbon atoms and are more preferably methyl or ethyl, most preferably methyl.

The present invention also provides compounds of formula (I) wherein:

$R^3$ is $C_{1-4}$alkyl and $R^1$, $R^2$ and n are as defined above; or $R^1$ is hydrogen; and n is 0;

$R^1$ represents hydrogen and $R^2$ represents one or more ring substituent(s) selected from:
hydroxy, fluorine, bromine or iodine;
$C_{3-6}$cycloalkyl optionally substituted by one or more substituents selected from halogen atoms and hydroxyl groups, or $C_{1-6}$alkoxy substituted by one or more substituents selected from halogen atoms and hydroxyl groups;
—$NR^4R^5$ where $R^4$ and $R^5$, which may be the same or different, each represent hydrogen or $C_{1-6}$alkyl;
—$S(O)_mR^6$, where m is 0, 1, 2 or 3 and $R^6$ represents hydrogen, $C_{1-6}$alkyl or $C_{3-6}$cycloalkyl;
—$SO_2NR^4R^5$ where $R^4$ and $R^5$ which may be the same or different, each represent $C_{1-6}$alkyl or one of $R^4$ and $R^5$ represents $C_{1-6}$alkyl and the other represents hydrogen;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$COR^7$ where $R^7$ is $C_{1-6}$alkyl; or $R^1$ represents one or more ring substituent(s) selected from:
fluorine, bromine, iodine or nitro;
$C_{1-6}$alkyl, $C_{3-6}$cycloalkyl optionally substituted by one or more substituents selected from halogen atoms and hydroxyl groups, or $C_{1-6}$alkoxy substituted by one or more substituents selected from halogen atoms and hydroxyl groups;
—$NR^4R^5$ where $R^4$ and $R^5$, which may be the same or different, each represent $C_{1-6}$alkyl or one of $R^4$ and $R^5$ represents $C_{1-6}$alkyl and the other represents hydrogen;
—$S(O)_mR^6$, where m is 0, 1, 2 or 3 and $R^6$ represents hydrogen, $C_{1-6}$alkyl or $C_{3-6}$cycloalkyl;
—$SO_2NR^4R^5$ where $R^4$ and $R^5$ each represent $C_{1-6}$alkyl or one of $R^4$ and $R^5$ represents $C_{1-6}$alkyl and the other represents hydrogen;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$COR^7$ where $R^7$ is $C_{1-6}$alkyl; and $R^2$ represents hydrogen; or $R^1$ and $R^2$ each represent one or more ring substituent(s) selected from:
hydrogen, hydroxy, halogen, cyano, nitro, $C_{1-6}$alkyl, $C_{3-6}$cycloalkyl or $C_{1-6}$alkoxy (where the alkyl or cycloalkyl moiety may be optionally substituted by one or more substituents selected from halogen atoms and hydroxyl groups);
—$NR^4R^5$ where $R^4$ and $R^5$, which may be the same or different, each represent hydrogen or $C_{1-6}$alkyl;
—$S(O)_mR^6$, where m is 0, 1, 2 or 3 and $R^6$ represents hydrogen, $C_{1-6}$alkyl or $C_{3-6}$cycloalkyl;
—$SO_2NR^4R^5$ where $R^4$ and $R^5$ are each as defined above;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$CO_2H$ or —$COR^7$ where $R^7$ is $C_{1-6}$alkyl or $C_{3-6}$cycloalkyl;
with the provisos that $R^1$ and $R^3$ do not both represent methoxy and that $R^2$ does not represent methyl when $R^1$ represents methoxy; or n is 1; and $R^1$ and $R^2$, which may be the same or different, each represent one or more ring substituent(s) selected from:
hydrogen, hydroxy, halogen, cyano, nitro, $C_{1-6}$alkyl, $C_{3-6}$cycloalkyl or $C_{1-6}$alkoxy (where the alkyl or cycloalkyl moiety may be optionally substituted by one or more substituents selected from halogen atoms and hydroxyl groups);
—$NR^4R^5$ where $R^4$ and $R^5$, which may be the same or different, each represent hydrogen or $C_{1-6}$alkyl;
—$S(O)_mR^6$, where m is 0, 1, 2 or 3 and $R^6$ represents hydrogen, $C_{1-6}$alkyl or $C_{3-6}$cycloalkyl;
—$SO_2NR_4R_5$ where $R^4$ and $R^5$ are each as defined above;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$CO_2H$ or —$COR^7$ where $R^7$ is $C_{1-6}$alkyl or $C_{3-6}$cycloalkyl;
with the proviso that $R^1$ does not represent methoxy; or
n is 2; and $R^1$ and $R^2$, which may be the same or different, each represent one or more ring substituent(s) selected from:
hydrogen, hydroxy, halogen, cyano, nitro, $C_{1-6}$alkyl, $C_{3-6}$cycloalkyl or $C_{1-6}$alkoxy (where the alkyl or cycloalkyl moiety may be optionally substituted by one or more substituents selected from halogen atoms and hydroxyl groups);
—$NR^4R^5$ where $R^4$ and $R^5$, which may be the same or different, each represent hydrogen or $C_{1-6}$alkyl;
—$S(O)_mR^6$, where m is 0, 1, 2 or 3 and $R^6$ represents hydrogen, $C_{1-6}$alkyl or $C_{3-6}$cycloalkyl;
—$SO_2NR_4R^5$ where $R^4$ and $R^5$ are each as defined above;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$CO_2H$ or —$COR^7$ where $R^7$ is $C_{1-6}$alkyl or $C_{3-6}$cycloalkyl;
with the provisos neither $R^1$ nor $R^2$ represent $SO_2NH_2$ or chlorine and that $R^1$ does not represent methoxy or hydroxy when $R^2$ represents chlorine;
or an ester, salt or other physiologically functional derivative thereof,
for use in therapy, more particularly for use as an antiviral agent.

According to one embodiment the invention provides compounds of formula (I) as defined immediately above in which $R^3$ represents hydrogen for use in therapy, more particularly for use as an antiviral agent.

Certain compounds of formula (I) are novel. According to a further aspect the invention provides compounds of formula (I) wherein:
$R^3$ is $C_{1-4}$alkyl and $R^1$, $R^2$ and n are as defined above; or
$R^1$ is hydrogen; and
n is 0; and
$R^1$ represents hydrogen and $R^2$ represents one or more ring substituent(s) selected from:
hydroxy;
$C_{3-6}$cycloalkyl optionally substituted by one or more substituents selected from halogen atoms and hydroxyl groups or $C_{1-6}$alkoxy substituted by one or more substituents selected from halogen atoms and hydroxyl groups;
—$NR^4R^5$ where $R^4$ and $R^5$, which may be the same or different, each represent $C_{1-6}$alkyl or one or $R^4$ and $R^5$ represents $C_{1-6}$ alkyl and the other represents hydrogen;
—$S(O)_mR^6$, where m is 0, 1, 2 or 3 and $R^6$ represents hydrogen, $C_{1-6}$alkyl or $C_{3-6}$cycloalkyl;

—$SO_2NHR^5$ where $R^5$ represents $C_{1-6}$alkyl;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$COR^7$ where $R^7$ is $C_{1-6}$alkyl or $C_{3-6}$cycloalkyl; or $R^1$ represents one or more ring substituent(s) selected from:
$C_{3-6}$cycloalkyl optionally substituted by one or more substituents selected from halogen atoms and hydroxyl groups or $C_{1-6}$alkoxy substituted by one or more substituents selected from halogen atoms and hydroxyl groups;
—$NR^4R^5$ where $R^4$ and $R^5$ each represent $C_{1-6}$alkyl or one of $R^4$ and $R^5$ represents $C_{1-6}$alkyl and the other represents hydrogen;
—$S(O)_mR^6$, where m is 0, 1, 2 or 3 and $R^6$ represents hydrogen, $C_{1-6}$alkyl or $C_{3-6}$cycloalkyl, except that $R^6$ does not represent methyl whem m is 0;
—$SO^2NR^4R^5$ where $R^4$ and $R^5$, which may be the same or different, each represent $C_{1-6}$alkyl or one of $R^4$ and $R^5$ represents $C_{1-6}$alkyl and the other represents hydrogen;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$COR^7$ where $R^7$ is $C_{1-6}$alkyl or $C_36$cycloalkyl; and
$R^2$ represents hydrogen; or $R^1$ and $R^2$ each represent one or more ring substituent(s) selected from:
hydroxy, halogen, cyano, nitro, $C_{1-6}$alkyl, $C_{3-6}$cycloalkyl or $C_{1-6}$alkoxy (where the alkyl or cycloalkyl moiety may be optionally substituted by one or more substituents selected from halogen atoms and hydroxyl groups);
—$NR^4R^5$ where $R^4$ and $R^5$, which may be the same or different, each represent hydrogen or $C_{1-6}$alkyl;
—$S(O)_mR^6$, where m is 0, 1, 2 or 3 and $R^6$ represents hydrogen, $C_{1-6}$alkyl or $C_{3-6}$cycloalkyl;
—$SO_2NR^4R^5$ where $R^4$ and $R^5$ are each as defined above;
phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and
—$CO_2H$ or —$COR^7$ where $R^7$ is $C_{1-6}$alkyl or $C_{3-6}$cycloalkyl;
with the provisos that $R^1$ and $R^2$ do not both represent methyl, methoxy, chlorine or bromine, $R^1$ does not represent chlorine when $R^2$ represents methyl, $R^1$ does not represent methoxy when $R^2$ represents chlorine or methyl; or
n is 1; and $R^1$ and $R^2$, which may be the same or different, each represent one or more ring substituent(s) selected from:
hydrogen, hydroxy, halogen, cyano, nitro, $C_{1-6}$alkyl, $C_{3-6}$cycloalkyl or $C_{1-6}$alkoxy (where the alkyl or cycloalkyl moiety may be optionally substituted by one or more substituents selected from halogen atoms and hydroxyl groups);
—$NR^4R^5$ where $R^4$ and $R^5$, which may be the same or different, each represent hydrogen or $C_{1-6}$alkyl;
—$S(O)_mR^6$, where m is 0, 1, 2 or 3 and $R^6$ represents hydrogen, $C_{1-6}$alkyl or $C_{3-6}$cycloalkyl;

—$SO_2NR^4R^5$ where $R^4$ and $R^5$ are each as defined above;

phenyl, phenyl$C_{1-3}$alkoxy or phenyl$C_{1-3}$alkyl where the phenyl group may be optionally substituted by one or more substituents independently selected from $C_{1-6}$alkyl, $C_{1-6}$alkoxy, hydroxy, nitro, halogen and amino; and —$CO_2H$ or —$COR^7$ where $R^7$ is $C_{1-6}$alkyl or $C_{3-6}$cycloalkyl;

with the provisos that $R^1$ and $R^2$ do not both represent hydrogen or methoxy; or n is 2; and $R^1$ and $R^2$, which may be the same or different, each represent one or more ring substituent(s) selected from:

hydrogen, hydroxy, halogen, cyano, nitro, $C_{1-6}$alkyl, $C_{3-6}$cycloalkyl or $C_{1-6}$alkoxy (where the alkyl or cycloalkyl moiety may be optionally substituted by one or more substituents selected from halogen atoms and hydroxyl groups);

—$NR^4R^5$ where $R^4$ and $R^5$, which may be the same or different, each represent hydrogen or $C_{1-6}$alkyl;

—$S(O)_mR^6$, where m is 0, 1, 2 or 3 and $R^6$ represents hydrogen, $C_{1-6}$alkyl or $C_{3-6}$cycloalkyl;

—$SO_2NR^4R^5$ where $R^4$ and $R^5$ are each as defined above;

phenyl, phenyl$C_{1-3}$alkoxy or phenyl$C_{1-3}$alkyl where the phenyl group may be optionally substituted by one or more substituents independently selected by one from $C_{1-6}$alkyl, $C_{1-6}$alkoxy, hydroxy, nitro, halogen and amino; and —$CO_2H$ or —$COR^7$ where $R^7$ is $C_{1-6}$alkyl or $C_{3-6}$cycloalkyl;

with the provisos that $R^1$ and $R^2$ do not both represent hydrogen, $R^1$ does not represent methyl, methoxy, chlorine or $SO_2NH_2$ when $R^2$ represents hydrogen, $R^2$ does not represent methyl, methoxy, chlorine or $SO_2NH_2$ when $R^1$ represents hydrogen and $R^1$ does not represent methoxy or a hydroxy group when $R^2$ represents chlorine;

or an ester, salt or other physiologically functional derivative thereof.

According to one embodiment the invention provides compounds of formula (I) as defined immediately above in which $R^3$ represents hydrogen.

Depending on the nature of the substituents $R^1$ and $R^2$, centres of optical and geometric isomerism may be introduced into the molecule. All optical and geometric isomers of compounds of formula (I) and mixtures thereof are embraced by the invention.

According to one preferred embodiment of the present invention, both $R^1$ and $R^2$ in formula (I) represent hydrogen atoms.

According to a preferred aspect of the invention $R^3$ in formula (I) represents a $C_{1-4}$alkyl group.

According to another preferred embodiment of the present invention, the compounds of formula (I) contain ring substituents $R^1$ or $R^2$, for example a single ring substituent, selected from halogen, more preferably fluorine or chlorine; nitro; $C_{1-6}$alkyl, more preferably $C_{1-3}$alkoxy, for example methyl; $C_{1-6}$alkoxy, more preferably $C_{1-3}$alkoxy, for example methoxy; halo$C_{1-6}$alkyl, more preferably halo$C_{1-3}$alkyl, for example trifluoromethyl; —$NR^4R^5$ where $R^4$ and $R^5$, which may be the same or different, each represent hydrogen or $C_{1-6}$alkyl, preferably hydrogen or $C_{1-3}$alkyl, more preferably both of $R^4$ and $R^5$ represent hydrogen or one represents hydrogen and the other represents methyl; —$SO_3H$; phenyl; phenyl$C_{1-3}$alkoxy, preferably phenylmethoxy; or —$CO_2H$.

Ring substituents $R^1$ or $R^2$ may be in any one of the 1-, 2-, 3-, 4-, 6-, 7-, 8- or 9-positions. Specific examples of single ring substituents are 1-, 3- or 4-fluoro, 7-chloro, 1-, 2-, 6-, 8- or 9-nitro, 1-, 2-, 6-, 7- or 9-methyl, 1- or 8-methoxy, 1-, 3-, 4- or 7-trifluoromethyl, 1-, 3-, 7- or 8-amino, 1-dimethylamino, 7-$SO_3H$, 7-phenyl, 1-phenylmethoxy, and 9-$CO_2H$.

Preferred compounds according to the present invention include:

dibenzothiazepin-11(10H)-one;

dibenzothiazepin-11(10H)-one-5,5-dioxide;

3-trifluoromethyldibenzothiazepin-11(10H)-one;

3-trifluoromethyldibenzothiazepin-11(10H)-one-5,5-dioxide;

4-trifluoromethyldibenzothiazepin-11(10H)-one;

4-trifluoromethyldibenzothiazepin-11(10H)-one-5-oxide;

4-trifluoromethyldibenzothiazepin-11(10H)-one-5,5-dioxide;

7-methoxydibenzothiazepin-11(10H)-one;

7-methoxydibenzothiazepin-11(10H)-one-5,5-dioxide;

8-trifluoromethyldibenzothiazepin-11(10H)-one;

8-trifluoromethyldibenzothiazepin-11(10H)-one-5,5-dioxide;

4-trifluoromethyl-9-methyldibenzothiazepin-11(10H)-one;

4-trifluoromethyl-9-methyldibenzothiazepin-11(10H)-one-5,5-dioxide;

10-ethyl-3-trifluoromethyldibenzothiazepin-11(10H)-one;

4-fluorodibenzothiazepin-11(10H)-one;

4-fluorodibenzothiazepin-11(10H)-one-5,5-dioxide;

10-methyl-4-fluorodibenzothiazepin-11-one;

10-methyl-4-trifluoromethyldibenzothiazepin-11-one;

4-methylthiodibenzothiazepin-11(10H)-one;

4-methylthiodibenzothiazepin-11(10H)-one-5,5-dioxide;

2-aminodibenzothiazepin-11(10H)-one;

2-nitrodibenzothiazepin-11(10H)-one;

2-nitrodibenzothiazepin-11(10H)-one 5,5-dioxide;

4,8-bistrifluoromethyldibenzothiazepin-11(10H)-one;

4,8-bistrifluoromethyldibenzothiazepin-11(10H)-one-5,5-dioxide;

1-methoxydibenzothiazepin-11(10H)-one;

1-methoxydibenzothiazepin-11(10H)-one-5,5-dioxide;

1-fluorodibenzothiazepin-11(10H)-one;

methyl dibenzothiazepin-11(10H)-one-3-carboxylate;

dibenzothiazepin-11(10H)-one-3-carboxylic acid;

and esters, salts and other physiologically functional derivatives thereof, more particularly acid addition salts thereof.

The compounds of formula (I) as defined above have been found to show antiviral activity in a number of assays, for example against Varicella-Zoster virus, Human cytomegalovirus, Human hepatitis virus, for example hepatitis B, and against Human T-cell lymphotropic viruses, especially HIV-1. Human T-cell of formula (I) may thus be useful in the treatment of a human or animal subject suffering from or liable to suffer from a viral infection. As used herein, reference to treatment includes both therapeutic and prophylactic treatment. The compounds of formula (I) may be particularly useful in the treatment of a human or animal subject suffering from or liable to suffer from a disorder associated with HIV infection, for example AIDS.

According to another aspect, the present invention provides a method of treatment of a human or animal subject suffering from or liable to suffer from a viral infection which comprises administering an effective amount of a compound of formula (I) or an ester, salt or other physiologically functional derivative thereof. According to a particular embodiment of this aspect of the invention, the viral infection is an HIV infection.

The present invention also provides a pharmaceutical composition for the treatment of a viral infection which comprises at least one compound of formula (I) or an ester, salt or other physiologically functional derivative thereof. The pharmaceutical composition is formulated in a manner suitable for use in human or veterinary medicine and for administration by any convenient route. The pharmaceutical composition will generally contain at least one physiologically acceptable carrier or excipient in addition to the active ingredient.

As used herein, the term "physiologically functional derivative" means any physiologically acceptable salt, ester, or salt of such ester, of a compound of formula (I) or any other compound which, upon administration to the recipient, is capable of providing (directly or indirectly) such a compound or an antivirally active metabolite or residue thereof.

Preferred esters of the compounds of formula (I) included within the scope of the present invention as physiologically functional derivatives include carboxylic acid esters in which the non-carbonyl moiety of the ester grouping is selected from straight or branched chain alkyl (for example methyl, n-propyl, n-butyl or t-butyl), cycloalkyl, alkoxyalkyl (for example methoxymethyl), aralkyl (for example benzyl), aryloxyalkyl (for example phenoxymethyl), aryl (for example phenyl optionally substituted by, for example, halogen, $C_{1-4}$alkyl, $C_{1-4}$alkoxy or amino): sulphonate esters such as alkyl- or alkylarylsulphonyl (for example methanesulphonyl); amino acid esters (for example L-valyl or L-isoleucyl); and mono-, di- or tri-phosphate esters. In such esters unless otherwise specified, any alkyl moiety present advantageously contains 1 to 18 carbon atoms, particularly 1 to 6 carbon atoms, more particularly 1 to 4 carbon atoms. Any cycloalkyl moiety present in such esters advantageously contains 3 to 6 carbon atoms. Any aryl moiety present in such esters advantageously comprises a phenyl group. Any reference to any of the above compounds also includes a reference to physiologically acceptable salts thereof.

Examples of physiologically acceptable salts of the compounds of formula (I) and physiologically acceptable derivatives thereof include salts derived from an appropriate base, such as alkali metal (for example sodium), alkaline earth metal (for example magnesium) salts, ammonium and $NX_4^+$ (wherein X is $C_{1-4}$alkyl). Physiologically acceptable salts of an hydrogen atom or an amino group include salts or organic carboxylic acids such as acetic, lactic, tartaric, malic, isethionic, lactobionic and succinic acids; organic sulfonic acids such as methanesulphonic, ethanesulphonic, benzenesulphonic and p-toluenesulphonic acids and inorganic acids such as hydrochloric, sulphuric, phosphoric and sulphamic acids. Physiologically acceptable salts of a compound of an hydroxy group include the anion of said compound in combination with a suitable cation such as $Na^+$, $NH_4^+$, $NX_4^+$ (wherein X is a $C_{1-4}$alkyl group).

For therapeutic use, salts of compounds of formula (I) will be physiologically acceptable, i.e. they will be salts derived from a physiologically acceptable acid or base. However, salts of acids or bases which are not physiologically acceptable may also find use, for example in the preparation or purification of the compound. All salts whether or not derived from a physiologically acceptable acid or base are to be considered as being within the scope of the present invention.

The compounds according to the invention may be employed in combination with other therapeutic agents for the treatment of viral infections or related conditions. Examples of such further therapeutic agents include other agents which are effective for the treatment of HIV infections or associated conditions such as 3'-azido-3'-deoxythymidine (zidovudine), other 2',3'-dideoxynucleosides such as 2',3'-dideoxycytidine, 2',3'-dideoxyadenosine and 2',3'-dideoxyinosine, carbovir, acyclic nucleosides (e.g. acyclovir), 2',3'-didehydrothymidine, chloro-TIBO, HEPT derivatives, Pentamidine, hydroxynaphthoquinones, phosphonate derivatives of nucleosides e.g. PMEA, interferons such as α-interferon, renal excretion inhibitors such as probenicid, nucleoside transport inhibitors such as dipyridamole, as well as immunomodulators such as interleukin II and granulocyte macrophage colony stimulating factors, erythropoetin, phosphonoformic acid and soluble $CD_4$ and genetically engineered derivatives thereof. The component compounds of such combination therapy may be administered simultaneously, in either separate or combined formulations, or at different times, e.g. sequentially, such that a combined effect is achieved.

The compounds of formula (I), also referred to herein as active ingredients, may be administered for therapy by any suitable route including oral, rectal, nasal, topical (including buccal and sublingual), vaginal, parenteral (including subcutaneous, intramuscular, intravenous and intradermal) and pulmonary. It will also be appreciated that the preferred route will vary with the condition and age of the recipient, the nature of the infection and the chosen active ingredient.

In general a suitable dose for treatment of a viral infection such as HIV is in the range of 0.5 to 120 mg per kilogram body weight of the recipient per day, preferably in the range of 1 to 90 mg per kilogram body weight per day and most preferably in the range 2 to 60 mg per kilogram body weight per day. The desired dose is preferably presented as two, three, four, five, six or more sub-doses administered at appropriate intervals throughout the day. These sub-doses may be administered in unit dosage forms, for example, containing 1 to 1500 mg, preferably 5 to 1000 mg, and most preferably 10 to 700 mg of active ingredient per unit dosage form.

Ideally, the active ingredient should be administered to achieve peak plasma concentrations of the active compound of from about 0.1 to about 100 μM, preferably about 0.5 to 70 μM, most preferably about 1 to about 50 μM. This may be achieved, for example, by the intravenous injection of a 0.1 to 5% solution of the active ingredient, optionally in saline, or orally administered, for example, as a tablet, capsule or syrup containing about 0.5 to about 100 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered alone it is preferable to present it as a pharmaceutical formulation comprising at least one compound of formula (I), together with one or more pharmaceutically acceptable carriers or excipients. The composition may optionally contain one or more other therapeutic agents. Each carrier and/or must be "acceptable" in the sense of being compatible with the other ingredients of the formulation and not injurious to the patient.

Formulations include those suitable for oral, rectal, nasal, topical (including buccal and sublingual), vaginal, parenteral (including subcutaneous, intramuscular, intravenous and intradermal) and pulmonary administration. The formulations may conveniently be presented in unit dosage form and may be prepared by any known methods in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, crossed-linked sodium carboxmethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example hydroxypropylmethyl cellulose in varying proportions to provide the desired release profile. Tablets may optionally be provided with an enteric coating, to provide release in parts of the gut other than the stomach.

Formulations suitable for topical administration in tho mouth include lozenges comprising the active ingredient in a flavoured basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, paste, gel, spray, aerosol or oil. Alternatively, a formulation may comprise a dressing such as a bandage or adhesive plaster impregnated with active ingredients and optionally one or more excipients or diluents. Carriers which may be used include for example polyhydric alcohols such as polyethylene glycols, propylene glycol or glycerol. Suitable excipients are those known in the art to be appropriate.

Formulations for rectal administration may be presented as suppository with a suitable base comprising for example cocoa butter or a salicylate.

Formulations suitable for vaginal administration may be presented as pessaries, tampons, creams, gels pastes, foams or spray formulations containing in addition to the active ingredient such carriers as are known in the art to be appropriate.

Formulations suitable for parenteral administration include aqueous and non-aqueous isotonic sterile injections solutions which may contain anti-oxidants, buffers, bacteriostats and solutes which render the formulation isotonic with the blood of the intended recipient: and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavouring agents.

The compounds according to the invention may also be presented for the use in the form of veterinary formulations, which may be prepared, for example, by methods that are conventional in the art.

According to another aspect, compounds of formula (I) may be prepared by the general methods outlined below. In the following description the symbols $R^1$, $R^2$ and n have the meanings ascribed to them in formula (I) unless otherwise stated.

According to a first general process (A) thiazepinones of formula (I) can be prepared by cyclisation of the corresponding 2-(2-carboxyphenylthio)aniline derivative of formula (II)

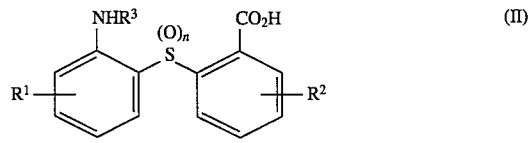

This process is particularly applicable to the production of compounds in which $R^3$ is hydrogen.

The reaction can be carried out at elevated temperature, for example 110° C. or above, more particularly 110° to 160° C., optionally in the presence of a suitable solvent, for example an inert solvent such as toluene, xylene or quinoline. For example, the reaction may be carried out in refluxing xylene fractions of boiling point 130° to 140° C. If desired the carboxylate group can be activated prior to the cyclisation, for example by the use of a reagent such as dicyclohexylcarbodiimide or a water soluble diimide.

According to a second general process (B), thiazepinones of formula (I) in which n is zero can be prepared by cyclisation of a compound of formula (III)

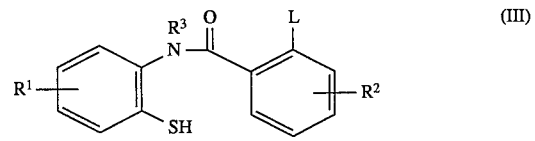

where L is a leaving group such as halogen, e.g. —F, —Cl, —Br or —I, —NO$_2$ or —SO$_2$R where R is alkyl or aryl. This process is particularly applicable to the production of compounds in which $R^3$ is hydrogen. The reaction may be carried out by treatment with base, for example sodium carbonate, triethylamine, 1,8-diazabicyclo[5,4,0]undec-7- ene or sodium hydride, in a suitable solvent such as tetrahydrofuran or dimethylformamide, optionally at elevated temperature, for example 60° to 120° C. Particularly in the case where the group L is halogen, the reaction may be carried out in the presence of a copper (Cu(0), Cu(I) or Cu(II)) catalyst.

According to a third general process (C), thiazepinones of formula (I) in which n is 1 or 2 can be prepared by treating the corresponding compound in which n is zero with an appropriate oxidising agent. Suitable oxidising agents include m-chloroperoxy benzoic acid (MCPBA), sodium perborate, $NO_2BF_4$ (J. Amer. Chem. Soc., 101, 5317 (1979)), ruthenium/alumina (Tet. Lett. 785 (1976)) and nitric acid (J. Org. Chem., 26, 1331 (1961)).

The conditions of the oxidation can be adjusted depending on the desired product. Thus, for example, a compound of formula (I) can be converted into the corresponding sulphoxide (n=1) by treatment with about 1 equivalent of MCPBA in a suitable solvent such as chloroform. The reaction can be carried out at room temperature and is complete in a relatively short period of say about half an hour. The corresponding sulphone (n =2) can be produced under similar conditions except that about 2 equivalents of MCPBA are used and the reaction is continued for a longer period of time, say about 24 hours. Alternatively a compound of formula (I) can be converted into the corresponding sulphone by treatment with an excess of sodium perborate in a suitable solvent, e.g. acetic acid.

According to a fourth general process (D) compounds of formula (I) in which $R^3$ represents $C_{1-4}$alkyl can be prepared by treating the corresponding compound of formula (I) in which $R^3$ represents hydrogen with an appropriate alkylating agent. Suitable alkylating agents include alkyl halides, for example alkyl iodides. The reaction may be carried out in the presence of base, for example sodium hydride, in a suitable solvent such as an amide, for example dimethylformamide at a temperature of for example 0° to 50° C., preferably ambient temperature.

Compounds of formula (II) can be prepared by hydrolysis of a corresponding 2-(2-aminophenylthio)-benzonitrile of formula (IV)

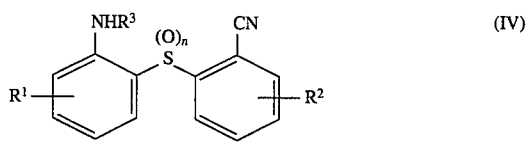
(IV)

Hydrolysis may be carried out in the presence of an acid, for example a mineral acid such as sulphuric acid, and/or an organic acid such as acetic acid. For example the reaction may be carried out in a 1:1:1 (v/v/v) mixture of acetic acid, water and conc sulphuric acid under reflux, for example for about 4 to 8 hours. Alternatively, the hydrolysis may be carried out in the presence of a base, such as an alkali metal hydroxide, e.g. sodium or potassium hydroxide. For example, the reaction may be carried out by refluxing in aqueous solution, for example over a period of about 4 to 14 hours.

Compounds of formula (IV) in which n is 1 or 2 may be prepared by oxidation of compounds of formula (IV) in which n is zero, for example under the conditions described above for the oxidation of compounds of formula (I) in which n is zero.

Compounds of formula (IV) can be prepared by treating the appropriate 2-aminothiophenol of formula (V) with the appropriate 2-fluorobenzonitrile of formula (VI).

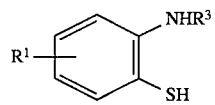
(V)

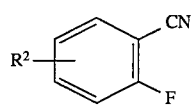
(VI)

The reaction may be carried out in the presence of base, for example an alkali metal hydride, alkali metal hydroxide, alkali metal alkoxide or pyridine, preferably in a suitable solvent, for example an ether such as tetrahydrofuran, an alcohol, dimethyl formamide, pyridine or water.

Where they are not already known, compounds of formula (V) can be prepared by standard methods (see for example Ann., 588, 29 (1947)).

Alternatively, compounds of formula (II) can be prepared by hydrolysis of the corresponding carboxylic acid ester of formula (VII)

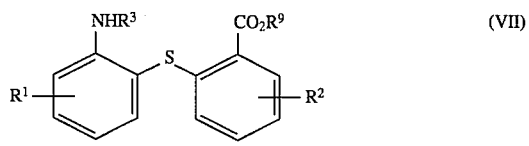
(VII)

where $R^9$ is an alkyl group, preferably ethyl. The reaction can be carried out under standard conditions for the hydrolysis of a carboxylic acid ester, for example treatment with a base such as sodium hydroxide in a suitable solvent such as aqueous ethanol. The reaction may be carried out at elevated temperature such as 80° to 100° C.

The ester of formula (VII) can be prepared by reaction of an appropriate 2-aminothiophenol (V) with an appropriate 2-fluorobenzoic acid ester (VIII)

(VIII)

under conditions analogous to those described above for the reaction of compounds of formulae (V) and (VI).

The ester of formula (VIII) can be prepared from the corresponding 2-fluorobenzoic acid by standard esterification techniques.

As a further alternative, compounds of formula (II) can be prepared by reaction of an appropriate 2-aminothiophenol (V) with a 2-iodobenzoic acid derivative of formula (IX).

(IX)

The reaction is preferably carried out in the presence of a base, for example an alkali metal hydroxide such as potassium hydroxide, and a cooper catalyst, e.g. Cu, CuO or CuCl. The reaction may be carried out in water at elevated temperature, e.g. about 100° C., or in a suitable organic solvent such as quinoline.

Compounds of formula (III) can be prepared by reaction of a suitable 2-aminothiophenol of formula (V) with a benzoic acid derivative of formula (X)

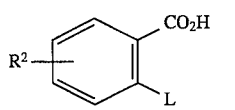

(X)

or an activated derivative thereof such as the corresponding acid chloride or anhydride. The reaction can be carried out in a suitable solvent such as pyridine at elevated temperature, e.g. about 100° C.

Where it is desired to isolate a compound of formula (I) as an acid addition salt, for example a physiologically acceptable acid addition salt, the salt may be formed by reacting the compound of formula (I) in the form of the free base with the appropriate acid. The two reactants are preferably used in equivalent amounts and the reaction may be carried out in a suitable solvent such as an alcohol, for example ethanol, an ester, for example ethyl acetate, or an ether, for example tetrahydrofuran. One salt of a compound of formula (I) may be converted into another salt using standard methods, for example where it is desired to convert a salt of a compound of formula (I) with an acid which is not physiologically acceptable into a salt with a physiologically acceptable acid.

The invention is further illustrated by the following examples.

EXAMPLE 1

3-Trifluoromethyl-10,11-dihydrodibenzo[b,f][1,4]thiazepin-11-one (a) 2-(2-Aminophenylthio)-4-trifluoromethylbenzonitrile 2-Aminothiophenol (8.17 g, 65 mmol) was added to a mixture of sodium hydride (2.35 g of 80% dispersion, 1.2 eq) in dimethylformamide (DMF, 100 ml) at 0° C. under a nitrogen atmosphere. After stirring for 30 mins 2-fluoro-4-trifluoromethylbenzonitrile (11.68 g, 0.95 eq) was added and the reaction mixture stirred at 0° C. for 1 hr then kept at 10° C. overnight. The solvent was evaporated in vaccuo and the residue taken up in ether (100 ml) and washed with sodium bicarbonate solution (1M, 100 ml). The organic layer was separated and dried (sodium sulphate, $Na_2SO_4$), and evaporated to give a yellow solid. The title compound (12.5 g, m.p. 102°–104° C., Rf 0.67, hexane/EtOAc 2:1) was obtained in pure form by chromatography on silica eluting first with hexane/ethyl acetate (6:1) then (4:1).

(b) 3-Trifluoromethyl-10,11-dihydrodibenzo[b,f][1,4]thiazepin-11-one 2-(2-Aminophenylthio)-4-trifluoromethylbenzonitrile (12.5 g, 42.5 mmol) in glacial acetic acid (135 ml), water (135 ml), and concentrated sulphuric acid (135 ml) was heated to 125°–130° C. for 2.5 hr before being cooled and added to 1.5 l of ice-water and adjusted to pH 4 with sodium hydroxide solution (10N, 480 ml). The product was extracted into chloroform (1 l), dried ($Na_2SO_4$) and evaporated in vacuo. The light brown oil was placed in xylene (800 ml) and refluxed for 18 hr in a Dean-Stark apparatus. The title compound was obtained as off-white crystals (7.8 g. m.p. 216°–217° C., Rf 0.28, hexane/EtOAc 2:1) after reducing the volume to approximately 450 ml and allowing the solution to cool.

EXAMPLE 2

3-Trifluoromethyl-10,11-dihydrodibenzo[b,f][1,4]thiazepin-11-one-5,5-dioxide (a) Metachloroperoxybenzoic acid (MCPBA, >2 eq) was added to a solution of the 3-trifluoromethyl-9,10-dihydrodibenzo [b,f][1,4]thiazepin-11-one (110 mg, 0.37 mmol) in dichloromethane and then stirred at room temperature overnight. Sodium bicarbonate (1M, 10 ml) and dichloromethane (10 ml) were added and the organic layer separated and dried ($Na_2SO_4$). Evaporation and chromatography on silica, eluting with cyclohexane/ethyl acetate, and trituration of the product with hexane/ethyl acetate (4:1) gave the title compound as an off-white powder (50 mg, m.p. 240°–241° C., Rf 0.5, hexane/EtOAc 1:1).

(b) 3-Trifluoromethyl-9,10-dihydrodibenzo [b,f][1,4]thiazepin-11-one (1.0 g, 3.39 mmol) was added to a solution of sodium perborate (4 eq) in acetic acid (25 ml) and heated at 70° C. for 4 hr. The reaction mixture was cooled, filtered and evaporated and water (30 ml) added to the residue. The title product was obtained as a white solid (1 g).

EXAMPLE 3

10,11-Dihydrodibenzo[b,f][1,4]thiazepin-11-one (a) 2-(2-Aminophenylthio)benzonitrile 2-Aminothiophenol (6.26 g, 50 mmol) was dissolved in dry THF (50 ml) and sodium hydride (2 g of 60% dispersion, 1 eq) added with stirring at 0° C. under nitrogen. After stirring for 0.5 hr this mixture was added portionwise to a stirred solution of 2-fluorobenzonitrile (1eq) in THF (30 ml). The mixture was allowed to warm to room temperature overnight and then evaporated in vacuo and the residue purified by chromatography on silica, eluting with dichloromethane. The title compound was obtained as an off-white solid (5.27 g).

(b) 10,11-Dihydrodibenzo[b,f][1,4]thiazepin-11-one 2-(2-Aminophenylthio)benzonitrile (3.72 g, 16 mmol) was dissolved in water (35 ml), acetic acid (35 ml) and concentrated sulphuric acid (35 ml) and stirred and heated under reflux for 3 hr. The mixture was allowed to cool and poured onto crushed ice (600 ml) and adjusted to pH 6 with sodium hydroxide solution (10N). The product was extracted into dichloromethane (700 ml), dried ($MgSO_4$) and evaporated in vacuo. The residue was dissolved in xylene (250 ml) and refluxed in a Dean-Stark apparatus for 72 hr. Filtration of the cold reaction mixture and recrystalisation from ethanol gave the title compound as a white crystals (2.99 g, m.p. 255°–256° C., Rf 0.68, $CH_2Cl_2$/MeOH 19:1).

EXAMPLE 4

10,11-Dihydrodibenzo[b,f][1,4]thiazepin-11-one-5-oxide

A solution of MCPBA (1 eq) in chloroform (5 ml) was added to a stirred solution of 10,11-dihydrodibenzo[b,f][1,4]thiazepin-11-one (114 mg, 0.5 mmol) in chloroform (30 ml). After 0.5 hr the reaction mixture was poured into sodium bicarbonate solution (5%, 30 ml), separated and the aqueous layer washed with chloroform (30 ml). The combined organic fractions were dried ($MgSO_4$) and evaporated. Recrystallisation from toluene gave the title compound as off-white crystals (76 mg, m.p. 308°–310° C., Rf 0.16, $CH_2Cl_2$/MeOH 50:1).

EXAMPLE 5

10,11-Dihydrodibenzo[b,f][1,4]thiazepin-11-one-5,5-dioxide

A solution of MCPBA (2 eq) in chloroform (5 ml) was added to a stirred solution of 10,11-dihydrodibenzo[b,f][1,4]thiazepin-11-one (114 mg, 0.5 mmol) in chloroform (35 ml). After stirring at room temperature for 26 hr the mixture was washed with saturated sodium bicarbonate solution (50 ml), water (50 ml), dried (MgSO$_4$) and evaporated. Recrystallisation from toluene gave the title compound as a white powder (88 mg, m.p. 284°–286° C., Rf 0.21, CH$_2$Cl$_2$/MeOH 50:1).

EXAMPLE 6

8-Trifluoromethyl-10,11-dihydrodibenzo[b,f][1,4]thiazepin-11-one

Using a procedure analagous to that of Example 3, 4-trifluoromethyl-2-aminothiophenol hydrochloride (11.48 g, 50 mmol) was combined with 2-fluorobenzonitrile in DMF as solvent (100 ml) to give crude 2-(4-trifluoromethyl-2-aminophenylthio) benzonitrile (6.84 g). Hydrolysis and subsequent condensation gave the title compound as off-white crystals from ethanol (1.1 g, m.p. 233°–235° C., Rf 0.21, CH$_2$Cl$_2$/MeOH 50:1).

EXAMPLE 7

4-Trifluoromethyl-10,11-dihydrodibenzo[b,f][1,4]thiazepin-11-one (a) 3-Trifluoromethyl-2-(2-aminophenylthio)benzonitrile Using a procedure analagous to that of Example 3(a), 2-aminothiophenol (6.26 g, 50 mmol) was combined with 3-trifluoromethyl-2-fluorobenzonitrile (1 eq) in DMF solvent (50 ml) to give the title compound as a white solid from cyclohexane (10.41 g).

(b) 4-Trifluoromethyl-10,11-dihydrodibenzo[b,f][1,4]thiazepin-11-one

3-Trifluoromethyl-2-(2-aminophenylthio)benzonitrile (7.36 g, 25 mmol) was dissolved in acetic acid (80 ml), water (80 ml) and concentrated sulphuric acid (80 ml) and the mixture stirred and heated under reflux for 5 hr, then at room temperature for 15 hr. The mixture was poured onto crushed ice (500 ml) and adjusted to pH 4 with sodium hydroxide (10N). The mixture was extracted with dichloromethane, dried (MgSO$_4$) and evaporated and the residue dissolved in hot xylene (500 ml). The mixture was heated under reflux for 21 hr in a Dean-Stark apparatus before being allowed to cool. After chromatography on silica (ethyl acetate/petrol eluant) and recrystallisation from cyclohexane the title compound was obtained as white crystals (3.99 g, m.p. 256°–258° C., Rf 0.44, petrol/EtOAc 1:1).

EXAMPLE 8

8-Trifluoromethyl-10,11-dihydrodibenzo[b,f][1,4]thiazepin-11-one-5,5-dioxide

A solution of MCPBA (>2 eq) in chloroform (30 ml) was added to a solution of the 8-trifluoromethyl-9,10-dihydrodibenzo [b,f][1,4]thiazepin-11-one (148 mg, 0.5 mmol). The mixture was stirred and refluxed for 12 hr, cooled, washed with saturated sodium bicarbonate, water and dried (MgSO$_4$). Evaporation and recrystallisation from toluene gave the title compound as colourless solid (0.22 g, m.p. 252.6°–254° C., Rf 0.85, petrol/EtOAc 1:2).

EXAMPLE 9

9-Methyl-4-trifluoromethyl-10,11-dihydrodibenzo[b,f][1,4]thiazepin-11-one (a) 4-Methyl-1,3-benzothiazole 4-Methyl-2-amino-1,3-benzothiazole (4.93 g, 30 mmol) was dissolved in phosphoric acid (85%, 200 ml) with warming and vigerous stirring. The solution was cooled (−10°) and aqueous sodium nitrite (12.42 g in 35 ml water) added with stirring and cooling to maintain the temperature below −4°. The resulting solution was added dropwise, with vigerous stirring, to a cooled solution of hypophosphorus acid (50% by weight, 75 ml) at 0°. The reaction mixture was allowed to warm to ambient temperature and when evolution of gas was complete the mixture was diluted with ice-water, neutralised with sodium carbonate and extracted with dichloromethane (about 2.5 litres). Evaporation of the organic extracts, after drying over magnesium sulphate, gave an orange oil that was purified by chromatography on silica (dichloromethane as eluant). The product with adequate purity for further reaction was obtained as a dark orange oil.

(b) 3-Trifluoromethyl-2-(3-methyl-2-aminophenylthio) benzonitrile

Impure 4-methyl-1,3-benzothiazole (3.5 g, approximately 23 mmol) was dissolved in aqueous ethanol (85%, 46 ml) and hydrazine hydrate solution (85%, 46 ml) added with stirring. The mixture was stirred at ambient temperature overnight before being evaporated and the residue azeotroped several times with toluene. The residue containing 3-methyl-2-aminothiophenol was combined with 3-trifluoromethyl-2-fluorobenzonitrile (4.72 g) in DMF (50 ml), using a procedure analagous to that of Example 3(a) to give the title compound as a fawn solid (2.53 g).

(c) 9-Methyl-4-trifluoromethyl-10,11-dihydrodibenzo [b,f][1,4]thiazepin-11-one

3-Trifluoromethyl-2-(3-methyl-2-aminophenylthio) benzonitrile (2.53 g, 8 mmol) was dissolved in acetic acid (25 ml), water (25 ml) and concentrated sulphuric acid (25 ml) and the mixture stirred and heated under reflux for 7.5 hours, then at ambient temperature for 15 hours before further sulphuric acid (25 ml) was added and the mixture stirred and heated under reflux for a further 8.5 hours. The mixture was allowed to stand at ambient temperature overnight then poured onto crushed ice (200 ml) and basified to pH 4 with aqueous sodium hydroxide (10N). The mixture was extracted with dichloromethane (3×200 ml) and the combined organic fractions dried (magnesium sulphate) and evaporated. The residue was dissolved in xylene (400 ml) and heated under reflux for 72 hours in a Dean-Stark apparatus, before being allowed to cool. After evaporation of the xylene, recrystallisation from toluene, followed by recrystallisation from ethanol, the title compound was obtained as an off-white solid (1.02 g, m.p. 273°–277°).

EXAMPLE 10

10-Methyl-4-trifluoromethyl-10,11-dihydrodibenzo[b,f][1,4]thiazepin-11-one

To a solution of 4-trifluoromethyl-10,11-dihydrodibenzo [b,f][1,4]thiazepin-11-one (0.295 g, 1 mmol) in DMF (20 ml) was added sodium hydride (0.1 g of 60% dispersion in oil) and the resulting mixture stirred for 30 minutes, before methyl iodide (1 equivalent) was added. After stirring for 1 hour the mixture was evaporated and the residue separated between ethyl acetate and aqueous sodium bicarbonate. The organic fractions were dried (magnesium sulphate) and evaporated. Purification of the residue by chromatography on silica, eluting with ethyl acetate/petrol (1:1, v/v), followed by recrystallisation from cyclohexane gave the title compound as colourless needles (0.121 g, m.p. 139°–141°, Rf 0.41 [silica, ethyl acetate/petrol, 1:2, v/v]).

EXAMPLE 11

2-Nitro-10,11-dihydrodibenzo[b,f][1,4]thiazepin-11-one (a) 2-(2-Aminophenylthio)-5-nitrobenzonitrile 2-Aminothiophenol (6.26 g, 50 mmol) was added to a mixture of sodium hydride (2.0 g of 60% oil dispersion, 50 mmol) in DMF (100 ml) at 0° under nitrogen. After stirring for 30 minutes at 0°, 2-fluoro-5-nitrobenzonitrile (8.3 g, 50 mmol) in DMF (20 ml) was added and the mixture kept at room temperature overnight. The reaction mixture was evaporated and azeotroped with toluene, then the residue was partitioned between chloroform and water and the layers separated. Drying (sodium sulphate) and evaporation of the organic layer gave a residue which was separated from chloroform as bright yellow crystals (10.1 g, Rf 0.52 in 1:1 ethyl acetate/hexane).

(b) 2-Nitro-10,11-dihydrodibenzo[b,f][1,4]thiazepin-11-one 2-(2-Aminophenylthio)-5-nitrobenzonitrile (8.5 g, 25 mmol) was dissolved in a mixture of glacial acetic acid (80 ml), concentrated sulphuric acid (100 ml) and water (80 ml) and then heated under reflux for 6 hours. The cooled mixture was added to ice water (500 ml) and brought to pH 4 by addition of 10N aqueous sodium hydroxide. Extraction with dichloromethane followed by filtration, drying (sodium sulphate) and evaporation of the organic layer afforded a residue which was put into xylene (500 ml) and refluxed for 15 hours with azeotropic removal of water. On cooling a brown powder deposited which was filtered off and purified by chromatography on silica gel eluting with 1:1 v/v ethyl acetate-hexane. Recrystallisation from ethanol gave the product as a greyish powder (2.80 g, m/s, $M^+$=272).

EXAMPLE 12

2-Nitro-10,11-dihydrodibenzo[b,f][1,4]thiazepin-11-one-5,5-dioxide

2-Nitro-10,11-dihydrodibenzo[b,f][1,4]thiazepin-11-one (0.27 g) in chloroform (30 ml) was stirred during the portionwise addition of m-chloroperbenzoic acid (0.44 g) then warmed at 60° for 3 days under nitrogen. The cooled solution was poured into aqueous sodium bicarbonate (100 ml) and the phases were separated. Evaporation of the dried organic layer gave a white residue which was recrystallised from ethanol to give the product (0.25 g, m/s, $M^+$=304).

EXAMPLE 13

2-Amino-10,11-dihydrodibenzo[b,f][1,4]thiazepin-11-one

2-Nitro-10,11-dihydrodibenzo[b,f][1,4]thiazepin-11-one (0.82 g) was dissolved in warm acetic acid (100 ml) and the resulting solution hydrogenated over Adam's catalyst (80 g) for 3 hours at atmospheric pressure. The catalyst was filtered off and the solution evaporated to dryness. Recrystallisation of the residue from methanol gave the product as a greenish powder (0.48 g, m/s, $M^+$=242).

EXAMPLE 14

(i) 4,8-Bis(trifluoromethyl)-10,11-dihydrodibenzo[b,f][1,4]thiazepin-11-one (a) 2-(2-Amino-4-trifluoromethylphenylthio)-3-trifluoromethylbenzonitrile 2-Amino-4-trifluoromethylthiophenol (5.74 g, 25 mmol) was added to a mixture of sodium hydride (2.0 g of 60% oil dispersion, 50 mmol) in DMF (100 ml) at 0° under nitrogen. After stirring for 30 minutes at 0°, 2-fluoro-3-trifluoromethylbenzonitrile (4.73 g, 25 mmol) in DMF (20 ml) was added and the mixture kept at room temperature overnight. The reaction mixture was evaporated and azeotroped with toluene, then the residue was partitioned between chloroform and water and the layers separated. Drying (magnesium sulphate) and evaporation of the organic layer gave a residue which was purified by chromatography on silica gel, eluting with dichloromethane. Recrystallisation from cyclohexane afforded the product as colourless needles (6.44 g).

(b) 4,8-Bis(trifluoromethyl)-10,11-dihydrodibenzo[b,f][1,4]thiazepin-11-one 2-(2-Amino-4-trifluoromethylphenylthio)-3-trifluoromethylbenzonitrile (5.43 g, 15 mmol) was dissolved in a mixture of glacial acetic acid (60 ml), concentrated sulphuric acid (55 ml) and water (60 ml) and then heated under reflux for 8 hours. The cooled mixture was added to ice water (500 ml) and brought to pH 4 by addition of 10N aqueous sodium hydroxide. Extraction with dichloromethane followed by filtration, drying (sodium sulphate) and evaporation of the organic layer afforded a residue which was put into xylene (500 ml) and refluxed for 72 hours with azeotropic removal of water. The resulting solution was evaporated and the residue was recrystallised twice from ethanol to give the product as colourless needles (4.30 g, m/s, $M^+$=363).

(ii) 9-Methyl-4-trifluoromethyl-10,11-dihydrobenzo[b,f][1,4]thiazepin-11-one Similarly prepared from 3-methyl-2-aminothiophenol. Product obtained from toluene as fawn needles (m/s, $M^+$=309).

(iii) 1-Methoxy-10,11-dihydrobenzo[b,f][1,4]thiazepin-11-one

Similarly prepared from 2-aminothiophenol and 2-fluoro-6-methoxybenzonitrile. Product obtained from ethanol as pale yellow crystals (m/s, $M^+$=258).

(iv) 4-Fluoro-10,11-dihydrobenzo[b,f][1,4]thiazepin-11-one

Similarly prepared from 2-aminothiophenol and 2,3-difluoro benzonitrile. Product obtained from ethanol as pale yellow crystals (m/s, $M^+$=245).

EXAMPLE 15

(i) 4,8-Bis(trifluoromethyl)-10,11-dihydrodibenzo[b,f][1,4]thiazepin-11-one-5,5-dioxide 4,8-Bis(trifluoromethyl)-10,11-dihydrodibenzo[b,f][1,4]thiazepin-11-one (0.54 g) in chloroform (100 ml) was stirred during the portionwise addition of m-chloroperbenzoic acid (0.90 g) then warmed to 50° for 4.5 hours under nitrogen. The cooled solution was poured into aqueous sodium bicarbonate (100 ml) and the phases were separated. Evaporation of the dried organic layer gave a white residue which was recrystallised from toluene and then from cyclohexane to give the product (0.20 g).

(ii) 9-Methyl-4-trifluoromethyl-10,11-dihydrobenzo[b,f][1,4]thiazepin-11-one-5,5-dioxide Similarly prepared from 9-methyl-4-trifluoromethyl-10,11-dihydrobenzo[b,f][1,4]thiazepin-11-one. Product obtained from methanol as colourless crystals (m.p. 304°–307°).

(iii) 1-Methoxy-10,11-dihydrobenzo[b,f][1,4]thiazepin-11-one-5,5-dioxide

Similarly prepared from 1-methoxy-10,11-dihydrobenzo[b,f][1,4]thiazepin-11-one. Product obtained from ethanol as colourless crystals (m/s, M$^+$=277).

EXAMPLE 16

3-Carboxy-10,11-dihydrobenzo[b,f][1,4]thiazepin-11-one

2-Aminothiophenol (5.01 g, 40 mmol) was added to a stirred mixture of 2-bromoterephthalic acid (4.90 g, 20 mmol), cuprous oxide (1.57 g, 11 mmol) and pyridine (2.0 g,) in quinoline (20 ml) and the resulting suspension was heated at 180° for 12 hours, after which it was cooled and stirred with concentrated hydrochloric acid (70 ml) for 30 minutes. The resulting solid was filtered off, washed with water and then crystallised from hot ethanol with the aid of charcoal to afford the product as colourless crystals (1.31 g, m.p. 300°–304°). The product was treated with methanol containing 2% acetyl chloride for 2 days at room temperature to give the corresponding methyl ester (m/s, M$^+$=285). A more pure sample of the free carboxy compound was obtained by base hydrolysis of the methyl ester.

EXAMPLE 17

(i) 4-Fluoro-10-methyl-10,11-dihydrobenzo[b,f][1,4]thiazepin-11-one

4-Fluoro-10,11-dihydrobenzo[b,f][1,4]thiazepin-11-one (0.50 g) in DMF (15 ml) was treated with sodium hydride 980% oil dispersion, 0.12 g) at 50°for 10 minutes under nitrogen. The solution was cooled to room temperature and methyl iodide was introduced. After a further 1 hour the solvent was removed by evaporation and the residue partitioned between ethyl acetate and dilute aqueous sodium bicarbonate. Evaporation of the dried organic layer gave a residue which was crystallised from ethanol/ethyl acetate to give the product as colourless crystals (0.25 g, m.p. 119°–121°).

(ii) 10-Ethyl-3-trifluoromethyl-10,11-dihydrobenzo[b,f][1,4]thiazepin-11-one Similarly prepared from 3-trifluoromethyl-9,10-dihydrobenzo[b,f][1,49 thiazepin-11-one and ethyl iodide. Product obtained from hot ethanol as white needles (m.p. 124°–125°).

EXAMPLE 18

10-Methyl-4-trifluoromethyl-10,11-dihydrobenzo[b,f][1,4]thiazepin-11-one-5,5-dioxide 10-Methyl-4-trifluoromethyl-10,11-dihydrobenzo[b,f][1,4]thiazepin-11-one (0.06 g) and m-chloroperbenzoic acid (0.17 g) were heated together in refluxing chloroform (5 ml) for 14 hours after which the mixture was cooled and shaken with dilute aqueous sodium bicarbonate. Evaporation of the dried (magnesium sulphate) layer afforded a white powder which was recrystallised from ethanol to give the product as fine needles (0.03 g, m/s, M$^+$=341).

EXAMPLE 19

4-Thiomethyl-10,11-dihydrodibenzo[b,f][1,4]thiazepin-11-one

A solution of 4-fluoro-10,11-dihydrodibenzo [b,f][1,4] thiazepin-11-one (600 mg, 2.4 mmol) and sodium thiomethoxide (410 mg, 3 equivalents) was heated in DMF (3 ml) at 60° for 60 hours. After cooling, the DMF was evaporated in vacuo, the residue taken up in methylene dichloride and washed with aqueous sodium bicarbonate (10%). After drying the organic layer (sodium sulphate) and evaporation, the residue was recrystallised from ethanol (twice) and then toluene to give the product (22 mg, m.p. 289°–290°, Rf 0.31 [silica, hexane/ethyl acetate, 2:1 v/v]).

EXAMPLE 20

10-Ethyl-3-trifluoromethyl-10,11-dihydrodibenzo[b,f][1,4]thiazepin-11-one-5,5-dioxide A solution of 10-ethyl-3-trifluoromethyl-10,11-dihydrodibenzo[b,f][1,4]thiazepin-11-one (300 mg. 0.93 mmol) and sodium perborate (570 mg, 4 equivalents) in acetic acid (7 ml) was heated at 70° for 4 hours. The mixture was cooled and filtered. Water (30 ml) was added to the filtrate, the white porecipitate isolated by filtration and dried in vacuo to give the product (m.p. 145°–146°).

EXAMPLE 21

7-Methoxy-10,11-dihydrodibenzo[b,f][1,4]thiazepin-11-one (a) 5-([2-Amino-5-methoxy)phenyl]-2-mercaptobenzoic acid To 2-amino-6-methoxy-1,3-benzthiazole (5 g, 0.027M) was added to a solution of potassium hydroxide (25 g in 50 ml of water). The mixture was heated at 140° for 5 hours. The crude 2-amino-5-methoxybenzenethiol produced was diluted with water (150 ml) and to this was added copper powder (1.25 g, 1 equivalent) and iodobenzoic acid (6.8 g, 1 equivalent). The mixture was heated under reflux for 4 hours under nitrogen. On cooling the mixture was filtered to remove copper, and acidified with concentrated hydrochloric acid. The solution was filtered to give the product as a light green solid (5 g).

(b) 7-Methoxy-10,11-dihydrodibenzo[b,f][1,4]thiazepin-11-one

To 5[(2-amino-5-methoxy)phenyl]-2-mercaptobenzoic acid (2 g, 8.3 mmol) in pyridine (50 ml) was added dimethylaminopropylcarbodiimide (1.68 g, 1.2 equivalents) and the mixture was heated under reflux for 1.5 hours. The pyridine was removed under reduced pressure, and the residue was washed with 10% hydrochloric acid, filtered, the solid washed with water and recrystallised from methanol to give the title compound as a blue solid (1.83 g, m.p. 232°–234°, Rf 0.51 [silica, cyclohexane/ethyl acetate, 1:1 v/v]).

EXAMPLE 22

7-Methoxy-10,11-dihydrodibenzo[b,f][1,4]thiazepin-11-one-5,5-dioxide

To 7-methoxy-10,11-dihydrodibenzo[b,f][1,4]thiazepin-11-one (1 g, 3.89 mmol) in acetic acid (15 ml) was added sodium perborate (2.4 g, 4 equivalents) and the mixture was heated under reflux for 5 hours. On cooling the perborate was filtered off, the acetic acid was removed under reduced pressure to give a white solid which was washed with water and recrystallised to give the title compound as a white solid (0.8 g, m.p. 244°–246°, Rf 0.59 [silica, cyclohexane/ethyl acetate, 1:1 v/v]).

Antiviral activity for compounds according to the invention can be demonstrated in vitro against HIV (MT4 assay) and in the HeLa-CD4+ plaque reduction assay. Results for a selection of the compounds of the invention are shown in the following table.

TABLE

| Compound of Example No. | HIV (in vitro) MT4 $IC_{50}$ (um) | HeLa-CD4 |
| --- | --- | --- |
| 5 | 13 | 4 |
| 7 | 2.5 | 8 |
| 10 | 2.8 | 7.3 |
| 14(iv) | 1.1 | 7.8 |
| 15(iv) | 1.8 | 4.7 |
| 17(i) | 0.7 | 16.5 |
| 19 | 2.3 | 1.6 |
| 22 | 12.8 | n/a |

Examples

The following examples illustrate pharmaceutical formulations according to the invention to which the active ingredient is a pharmaceutically acceptable compound according to the invention.

Example 23

Tablet Formulations

The following formulations A, B and C are prepared by wet granulation of the ingredients with a solution of povidone, followed by addition of the magnesium stearate and compression.

Formulation A

|  | mg/tablet | mg/tablet |
| --- | --- | --- |
| (a) Active ingredient | 250 | 250 |
| (b) Lactose B.P. | 210 | 26 |
| (c) Povidone B.P. | 15 | 9 |
| (d) Sodium Starch Glycollate | 20 | 12 |
| (e) Magnesium Stearate | 5 | 3 |
|  | 500 | 300 |

Formulation B

|  | mg/tablet | mg/tablet |
| --- | --- | --- |
| (a) Active ingredient | 250 | 250 |
| (b) Lactose | 150 | — |
| (c) Avicel PH 101 | 60 | 26 |
| (d) Povidone B.P. | 15 | 9 |
| (e) Sodium Starch Glycollate | 20 | 12 |
| (f) Magnesium Stearate | 5 | 3 |
|  | 500 | 300 |

Formulation C

|  | mg/tablet |
| --- | --- |
| Active ingredient | 100 |
| Lactose | 200 |
| Starch | 50 |
| Povidone | 5 |
| Magnesium stearate | 4 |
|  | 359 |

The following formulations, D and E, are prepared by direct compression of the admixed ingredients.

Formulation D

|  | mg/capsule |
| --- | --- |
| Active Ingredient | 250 |
| Pregelatinised Starch NF15 | 150 |
|  | 400 |

Formulation E

|  | mg/capsule |
| --- | --- |
| Active Ingredient | 250 |
| Lactose | 150 |
| Avicel | 100 |
|  | 500 |

Formulation F (Controlled Release Formulation)

The formulation is prepared by wet granulation of the following ingredients with a solution of povidone followed by addition of the magnesium stearate and compression.

|  | mg/tablet |
| --- | --- |
| (a) Active Ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
|  | 700 |

Drug release takes place over a period of about 6–8 hours and is complete after 12 hours.

Example 24

Capsule Formulations

Formulation A

A capsule formulation is prepared by admixing the ingredients of Formulation D in Example 3 above and filling into two-part hard gelatin capsule.

Formulation B

| | mg/capsule |
|---|---|
| (a) Active ingredient | 250 |
| (b) Lactose B.P. | 143 |
| (c) Sodium Starch Glycollate | 25 |
| (d) Magnesium Stearate | 2 |
| | 420 |

Capsules are prepared by admixing the above ingredients and filling into two-part hard gelatin capsules.

Formulation C

| | mg/capsule |
|---|---|
| (a) Active ingredient | 250 |
| (b) Macrogol 4000 BP | 350 |
| | 600 |

Capsules are prepared by melting the Macrogol 4000 BP, dispersing the active ingredient in the melt and filling the melt into two-part hard gelatin capsules.

Formulation D

| | mg/capsule |
|---|---|
| Active ingredient | 250 |
| Lecithin | 100 |
| Arachis Oil | 100 |
| | 450 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients (a), (b) and (c) using an extruder, followed by spheronisation of the extrudate and drying. The dried pellets are then coated with the release-controlling membrane (d) and filled into two-piece, hard gelatin capsules.

| | mg/capsule |
|---|---|
| (a) Active Ingredient | 250 |
| (b) Microcrystalline Cellulose | 125 |
| (c) Lactose BP | 125 |
| (d) Ethyl Cellulose | 13 |
| | 513 |

Example 25

Injectable Formulation

Formulation A

| | |
|---|---|
| Active ingredient | 0.200 g |
| Hydrochloric acid solution, 0.1M | q.s. to pH 4.0 to 7.0 |
| Sodium hydroxide solution, 0.1M | q.s. to pH 4.0 to 7.0 |
| Sterile water | q.s. to 10 ml |

The active ingredient is dissolved in most of the water (35°–40° C.) and the pH adjusted to between 4.0 and 7.0 using the hydrochloric acid or the sodium hydroxide as appropriate. The batch is then made up to volume with the water and filtered through a sterile micropore filter into a sterile amber glass vial 10 ml and sealed with sterile closures and overseals.

Formulation B

| | |
|---|---|
| Active ingredient | 0.125 g |
| Sterile, pyrogen-free, pH 7 phosphate buffer, | q.s. to 25 ml |

Example 26

Intramuscular injection

| | | |
|---|---|---|
| Active Ingredient | | 0.20 g |
| Benzyl Alcohol | | 0.10 g |
| Glycofurol 75 | | 1.45 g |
| Water for Injection | q.s. to | 3.00 ml |

The active ingredient is dissolved in the glycofurol. The benzyl alcohol is then added and dissolved, and water added to 3 ml. The mixture is then filtered through a sterile micropore filter and sealed in sterile amber glass vials 3 ml.

Example 27

Syrup

| | | |
|---|---|---|
| Active ingredient | | 0.25 g |
| Sorbitol Solution | | 0.10 g |
| Glycerol | | 2.00 g |
| Sodium Benzoate | | 0.005 g |
| Flavour, Peach 17.42.3169 | | 0.0125 ml |
| Purified Water | q.s. to | 5.00 ml |

The active ingredient is dissolved in a mixture of the glycerol and most of the purified water. An aqueous solution of the sodium benzoate is then added to the solution, followed by addition of the sorbitol solution and finally the flavour. The volume is made up with purified water and mixed well.

Example 28

Suppository

| | mg/suppository |
|---|---|
| Active ingredient | 250 |
| Hard Fat, BP (Witepsol H15 - Dynamit Nobel) | 1770 |
| | 2020 |

One-fifth of the Witepsol H15 is melted in a steam-jacketed pan at 45° C. maximum. The active ingredient is sifted through a 200 μm sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.0 g of the mixture is filled into suitable, 2 ml plastic moulds. The suppositories are allowed to cool to room temperature.

Example 29

Pessaries

|  | mg/pessary |
|---|---|
| Active ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

We claim:

1. A method for treating a viral infection comprising administering to a subject in need of same an antiviral effective amount of a compound of formula (I)

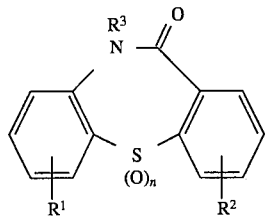

wherein:

n is 0, 1 or 2; and $R^1$ and $R^2$, which may be the same or different, each represent one or more ring substituent(s) selected from: halogen; nitro; $C_{1-6}$alkyl; halo$C_{1-6}$alkyl; $C_{1-6}$alkoxy; —$NR^4R^5$ where $R^4$ and $R^5$, which may be the same or different, each represent hydrogen or $C_{1-6}$alkyl; —$SO_3H$; phenyl; phenyl$C_{1-3}$alkoxy; and —$CO_2H$;

$R^3$ represents hydrogen or $C_{1-4}$alkyl; or an ester, salt or salt of such an ester thereof.

2. A method according to claim 1 wherein $R^3$ is hydrogen.

3. A method according to claim 1 wherein the compound of formula (I) is selected from the group consisting of:

3-trifluoromethyldibenzothiazepin-11(10H)-one;
3-trifluoromethyldibenzothiazepin-11(10H)-one-5,5-dioxide;
4-trifluoromethyldibenzothiazepin-11(10H)-one;
4-trifluoromethyldibenzothiazepin-11(10H)-one-5-oxide;
4-trifluoromethyldibenzothiazepin-11(10H)-one-5,5-dioxide;
7-methoxydibenzothiazepin-11(10H)-one;
7-methoxydibenzothiazepin-11(10H)-one-5,5-dioxide;
8-trifluoromethyldibenzothiazepin-11(10H)-one;
8-trifluoromethyldibenzothiazepin-11(10H)-one-5,5-dioxide;
4-trifluoromethyl-9-methyldibenzothiazepin-11(10H)-one;
4-trifluoromethyl-9-methyldibenzothiazepin-11(10H)-one-5,5-dioxide;
10-ethyl-3-trifluoromethyldibenzothiazepin-11(10H)-one;
4-fluorodibenzothiazepin-11(10H)-one;
4-fluorodibenzothiazepin-11(10H)-one-5,5-dioxide;
10-methyl-4-fluorodibenzothiazepin-11-one;
10-methyl-4-trifluoromethyldibenzothiazepin-11-one;
4-methylthiodibenzothiazepin-11(10H)-one;
4-methylthiodibenzothiazepin-11(10H)-one-5,5-dioxide;
2-aminodibenzothiazepin-11(10H)-one;
2-nitrodibenzothiazepin-11(10H)-one;
2-nitrodibenzothiazepin-11(10H)-one-5,5-dioxide;
4,8-bistrifluoromethyldibenzothiazepin-11(10H)-one;
4,8-bistrifluoromethyldibenzothiazepin-11(10H)-one-5,5-dioxide;
1-methoxydibenzothiazepin-11(10H)-one;
1-methoxydibenzothiazepin-11(10H)-one-5,5-dioxide;
1-fluorodibenzothiazepin-11(10H)-one;
methyl dibenzothiazepin-11(10H)-one-3-carboxylate;
dibenzothiazepin-11(10H)-one-3-carboxylic acid;
and esters, salts and salts of such an ester thereof.

4. A compound of formula (I)

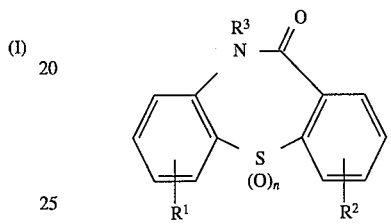

wherein:

$R^3$ is $C_{1-4}$alkyl; and $R^1$ and $R^2$, which may be the same or different, each represent one or more ring substituent(s) selected from: halogen; nitro; $C_{1-6}$alkyl; halo$C_{1-6}$alkyl; $C_{1-6}$alkoxy; —$NR^4R^5$ where $R^4$ and $R^5$, which may be the same or different, each represent hydrogen or $C_{1-6}$alkyl; —$SO_3H$; phenyl; phenyl$C_{1-3}$alkoxy; and —$CO_2H$;

or an ester, salt or salt of such an ester thereof.

5. A compound according to claim 4 selected from a group consisting of:

3-trifluoromethyldibenzothiazepin-11(10H)-one;
3-trifluoromethyldibenzothiazepin-11(10H)-one-5,5-dioxide;
4-trifluoromethyldibenzothiazepin-11(10H)-one;
4-trifluoromethyldibenzothiazepin-11(10H)-one-5-oxide;
4-trifluoromethyldibenzothiazepin-11(10H)-one-5,5-dioxide;
7-methoxydibenzothiazepin-11(10H)-one;
7-methoxydibenzothiazepin-11(10H)-one-5,5-dioxide;
8-trifluoromethyldibenzothiazepin-11(10H)-one;
8-trifluoromethyldibenzothiazepin-11(10H)-one-5,5-dioxide;
4-trifluoromethyl-9-methyldibenzothiazepin-11(10H)-one;
4-trifluoromethyl-9-methyldibenzothiazepin-11(10H)-one-5,5-dioxide;
10-ethyl-3-trifluoromethyldibenzothiazepin-11(10H)-one;
4-fluorodibenzothiazepin-11(10H)-one;
4-fluorodibenzothiazepin-11(10H)-one-5,5-dioxide;
10-methyl-4-fluorodibenzothiazepin-11-one;
10-methyl-4-trifluoromethyldibenzothiazepin-11-one;
4-methylthiodibenzothiazepin-11(10H)-one;
4-methylthiodibenzothiazepin-11(10)-one-5,5-dioxide;

2-aminodibenzothiazepin-11(10H)-one;
2-nitrodibenzothiazepin-11(10H)-one;
2-nitrodibenzothiazepin-11(10H)-one-5,5-dioxide;
4,8-bistrifluoromethyldibenzothiazepin-11(10H)-one;
4,8-bistrifluoromethyldibenzothiazepin-11(10H)-one-5,5-dioxide;
1-methoxydibenzothiazepin-11(10H)-one;
1-methoxydibenzothiazepin-11(10H)-one-5,5-dioxide;
1-fluorodibenzothiazepin-11(10H)-one;
methyl dibenzothiazepin-11(10H)-one-3-carboxylate;
dibenzothiazepin-11(10H)-one-3-carboxylic acid;
and esters, salts and salts of such esters thereof.

6. A pharmaceutical composition which comprises at least one compound of claim 4 together with at least one physiologically acceptable carrier or excipient.

* * * * *